United States Patent
Muehlegger et al.

(10) Patent No.: US 6,573,374 B1
(45) Date of Patent: Jun. 3, 2003

(54) NUCLEOTIDES LABELLED WITH AN INFRARED DYE AND THEIR USE IN NUCLEIC ACID DETECTION

(75) Inventors: Klaus Muehlegger, Polling (DE); Hans-Joachim Hoeltke, Tutzing (DE); Christian Birkner, Uffing (DE); Herbert Von Der Eltz, Weilheim (DE)

(73) Assignee: Boehringer Mannheim GmbH, Mannheim (DE)

( * ) Notice: Subject to any disclaimer, the term of this patent is extended or adjusted under 35 U.S.C. 154(b) by 0 days.

(21) Appl. No.: 08/411,761

(22) PCT Filed: Jul. 30, 1994

(86) PCT No.: PCT/EP94/02541

§ 371 (c)(1), (2), (4) Date: Mar. 28, 1995

(87) PCT Pub. No.: WO95/04747

PCT Pub. Date: Feb. 16, 1995

(30) Foreign Application Priority Data

Aug. 6, 1993 (DE) .......................................... 43 26 466

(51) Int. Cl.$^7$ .............................................. C07H 19/04
(52) U.S. Cl. .................. 536/26.26; 536/23.1; 536/24.3; 536/25.32; 536/26.6; 536/26.7; 536/26.8; 435/6
(58) Field of Search ............................ 435/6; 536/24.3, 536/25.32, 26.6, 26.7, 26.8, 23.1

(56) References Cited

U.S. PATENT DOCUMENTS

| 4,828,979 A | * | 5/1989 | Klevan et al. ............... 435/6 |
| 5,047,519 A | * | 9/1991 | Hobbs, Jr. et al. ........ 536/25.32 |
| 5,151,507 A | | 9/1992 | Hobbs, Jr. et al. |

FOREIGN PATENT DOCUMENTS

DE 39 12 040 A1 3/1990

OTHER PUBLICATIONS

Kessler entitled "Nonradioactive Labeling and Detection of –Biomolecules", Springer Verlag, Berlin, Heidelberg (1992).

Hoeltke et al., *Biol. Chem. Hoppe–Seyler*, 371:929 (1990).
Feinberg et al.., *Anal. Biochem.*, 137:266 (1984).
Rigby et al., *J. Mol. Biol.*, 113:237 (1977).
Mujumdar et al., "Cyanine Dye Labeling Reagents: Sulfoindocyanine Succinimidyl Esters", Bioconjugate Chemistry, vol. 4, No. 2, pp. 105–111 (Mar./Apr. 1993).
Southwick et al., "Cyanine Dye Labeling Reagents –Carboxymethylindocyanine Succinimidyl Esters", Cytometry, vol. 11, pp. 418–430 (1990).
Ernst et al., "Cyanine Dye Labeling Reagents for Sulfhydryl Groups", Cytometry, vol. 10, pp. 3–10 (1989).
Gebeyehu et al., "Novel biotinylated nucleotide –analogs for labeling and colorimetric detection of DNA", Nucleic Acids Research, vol. 15, pp. 4513–4534 (1987).

* cited by examiner

*Primary Examiner*—James O. Wilson
(74) *Attorney, Agent, or Firm*—Fulbright & Jaworski LLP

(57) ABSTRACT

Nucleoside-5'-triphosphates and phosphoramidites which carry a residue absorbing in the long wavelength region, preferably a carbocyanine group of the general formula (I), on the base portion or on the phosphorus atom

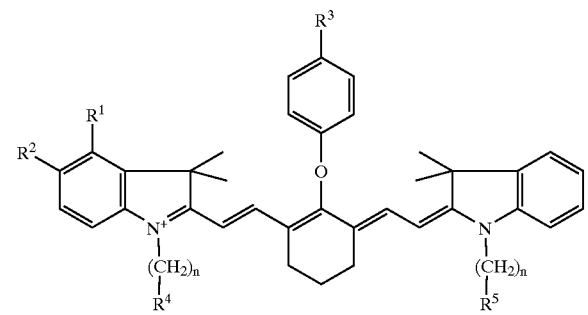

in which $R^1$ and $R^2$ each denote hydrogen or together form a phenyl residue; $R^3$ denotes hydrogen if linkage with the nucleotide is via the $R^4$ position or it denotes a —NHCS— group if linkage with the nucleotide is via the $R^3$ position; both $R^4$ and $R^5$, or $R^5$, alone denote an alkylsulfonyl group with n being a number from 3 to 5 or $R^4$ represents a —NHCS— group with n being a number from 3 to 8, as well as the use of the compounds to label, detect and sequence nucleic acids.

14 Claims, No Drawings

NUCLEOTIDES LABELLED WITH AN INFRARED DYE AND THEIR USE IN NUCLEIC ACID DETECTION

FIELD OF THE INVENTION

The invention concerns nucleoside-5'-triphosphates and phosphoramidites which carry a fluorescent residue absorbing in the long wavelength range, preferably a carbocyanine group, on the base portion or on the phosphorus atom, as well as their use for labelling, detecting and sequencing nucleic acids.

BACKGROUND OF THE INVENTION

Nucleic acids are of crucial importance in living nature as carriers or transferrers of genetic information. Since their discovery by F. Miescher they have therefore stimulated a broad scientific interest which has led to the elucidation of their function, structure and mechanism of action. with increasing knowledge of these fundamental molecular biological mechanisms it has in recent years become possible to pursue the new combination of genes. This technology opens for example new possibilities in medical diagnosis and therapy and in plant breeding.

An essential tool for understanding these interrelations and solving the problems was and is the detection of nucleic acids and their sequences i.e. their primary structure.

The specific detectability of nucleic acids is based on the properties of these molecules to interact, i.e. to hybridize, with other nucleic acids by forming base pairs via hydrogen bridges. Nucleic acids (probes) labelled in a suitable manner, i.e. provided with indicator groups, can thus be used to detect complimentary nucleic acids (target).

The determination of the primary structure (sequence), i.e. the sequence of the heterocyclic bases, of a nucleic acid is carried out by means of sequencing techniques. This knowledge of the sequence is in turn a prerequisite for a targetted and specific use of nucleic acids in molecular biological investigations and working techniques. The sequencing finally also utilizes the principle of specific hybridization of nucleic acids among each other. As mentioned above, labelled nucleic acid fragments are also used for this.

It is clear from the aforementioned that suitable labelling of nucleic acids is an essential prerequisite for any method of detection.

Above all, radioactive labelling with suitable isotopes such as $^{32}p$ or $^{35}S$ is already being used for this at an early stage. The disadvantages of using radioactive reagents are, however, obvious: such work requires special room installations and permits, as well as a controlled and complicated disposal of the radioactive waste. The reagents for radioactive labelling are expensive. A longer storage of such labelled samples is not possible due to the short half-life of the above nuclides.

Therefore in recent years there have been attempts to circumvent these serious disadvantages i.e. to get away from radioactive labelling. In doing so the high sensitivity of this type of labelling should be preserved as far as possible. Great advances have in fact been made in this case [see e.g. Nonradioactive Labeling and Detection of Biomolecules, C. Kessler (Editor), "Springer Verlag Berlin, Heidelberg" 1992].

Haptens (such as biotin or digoxigenin), enzymes (such as alkaline phosphatase or peroxidase) or fluorescent dyes (such as fluorescein or rhodamine) have above all proven to be successful among others as non-radioactive indicator molecules.

Although labelling with haptens such as e.g. digoxigenin extends into the sensitivity range of radioactivity, a direct detection of hapten-labelled nucleic acids analogous to radioactive labelling is not possible. A subsequent detection reaction is necessary which is, for example, achieved by means of an antibody reaction. This indirect detection requires several steps i.e. more time and financial expense. Since proteins are used for the detection reaction, a special treatment of the solid phase (membranes, microtitre plates) by blocking and washing steps is necessary in order to reduce unspecific binding. Despite this, the sensitivity of this two-step detection is usually limited due to the occurrence of interfering background colouration resulting from unspecific protein binding. The same basically applies to direct enzyme-labelled nucleic acids.

The said disadvantage of the aforementioned indirect detection does not occur when using fluorescent-labelled nucleic acids. A direct detection is possible by exciting the fluorescence and can be visualized and measured with a suitable device (fluorescence microscope, scanner). However, the autofluorescence of cell and tissue components of the biological material to be examined such as dyes, lipids, proteins etc. also interferes in this case. Such interferences also occur particularly when using solid carrier materials (e.g. nylon membranes) due to their intrinsic fluorescence and complicate or prevent the detection.

In principle a solution to these problems is to use dyes whose excitation and emission is in wavelength ranges above 680 nm i.e. in the near infrared (NIR) range. The aforementioned interfering influences are not significant under these circumstances. A further important advantage is that very durable cheap laser diodes can be used for the excitation.

Thus for example the technique of DNA sequencing by photoelectric measurement with a laser and a sensor after fluorescent labelling of the DNA fragments is the subject matter of an application U.S. Pat. No. 4,729,947. In this method, oligonucleotides labelled with an IR dye are used in a known manner as a primer in the so-called Sanger method which act in this process as starters for the synthesis of the new complementary nucleic acid strand. However, a disadvantage of this method is that—depending on the DNA to be sequenced—specific labelled primers have in each case to be newly synthesized again and again i.e. numerous such labelled primers. This synthesis of labelled oligomeric primers is expensive and time-consuming since the unlabelled oligonucleotide has to be synthesized at first and subsequently the signal (reporter) group is chemically attached in a second reaction.

The object of the present invention is therefore to produce compounds which enable a universal, simple and specific labelling of nucleic acids.

It is now known that nucleic acids can be newly synthesized and concomitantly labelled by the incorporation of appropriately labelled nucleoside triphosphates using polymerases. In the field of deoxyribonucleic acids (DNA) this is achieved by DNA polymerases using the methods of nick translation [Rigby, P. W. et al. (1977) J. Mol. Biol. 113, 237] and of random primed labelling [Feinberg, A. P. & Vogelstein, B. (1984) Anal. Biochem. 137, 266] by incorporating deoxynucleotides and in the case of ribonucleic acids by RNA polymerases and ribonucleotides along the lines of a transcription. A further method of labelling nucleic acids is by means of a so-called 3' tailing reaction with the aid of terminal transferase and ribo or deoxyribonucleoside triphosphates.

However, nucleoside triphosphates provided with indicator molecules such as fluorescein or digoxigenin (MW 332 or 390) are—in contrast to their natural substrates—accepted relatively poorly as substrates by polymerases and incorporated relatively poorly into the newly synthesized nucleic acid (Hoeltke, H.-J. et al. (1990) Biol. Chem. Hoppe-Seyler 371, 929).

It is therefore not to be expected that indicator molecules with even considerably higher molecular weights (800–1000) would be accepted by polymerases as substrates and incorporated into nucleic acids. It is even less likely that these molecules with their given spatially demanding structure would be converted by polymerases due to strong steric hindrance.

Surprisingly it has been found that nucleoside triphosphates labelled with infrared dyes are accepted as substrates by polymerases such as T7 DNA polymerase and are incorporated into nucleic acids. The compounds according to the invention are therefore novel.

A further object of the invention is to provide a method of using the aforementioned labelled nucleotides according to the invention which enable nucleic acids labelled thus to be detected directly on solid carriers such as e.g. nylon membranes or in solution such as e.g. in microtitre plates.

As already described above, a disadvantage of labelling nucleic acids with fluorophores such as fluorescein or tetramethylrhodamine is that the intrinsic fluorescence of the carrier material interferes with the measurement of this fluorescence.

If, however, the nucleoside triphosphates labelled with IR dye according to the invention are used to label nucleic acids, these interferences are no longer significant because the measurement wavelength is located in the near infrared range.

The advantages of a nucleic acid detection by in situ hybridization are known. In this method the labelled samples or probes are either detected directly under a fluorescence microscope or, in the case of hapten labelling, are detected in an immunological reaction (ELISA) by means of a further process step. This visualization is usually achieved by immobilizing the samples for example on a nylon membrane or in a liquid homogeneous phase in microtitre plates. This additional step is very time-consuming and costly. It is thus desirable to omit this step.

SUMMARY OF THE INVENTION

In the instant invention, the possibility of directly exciting the IR-fluorescent-labelled nucleic acids by suitable laser diodes and the aforementioned insensitivity of the detection towards autofluorescence of the carrier material enables simple and cost-effective equipment to be used. The immunological detection reaction can be omitted. The IR-labelled nucleic acid is simply detected by optical means through a laser/detector combination with the aid of a suitable scanner or microtitre plate reader.

The use of the nucleoside 5'-triphosphates labelled with infrared fluorophores as polymerase substrates enables direct enzymatic incorporation into nucleic acids and detection of the nucleic acids labelled in this manner for sequencing, and it also allows an in situ hybridization which is also part of the invention.

DETAILED DESCRIPTION OF THE INVENTION

The nucleoside 5'-triphosphates of the invention are of the general formula

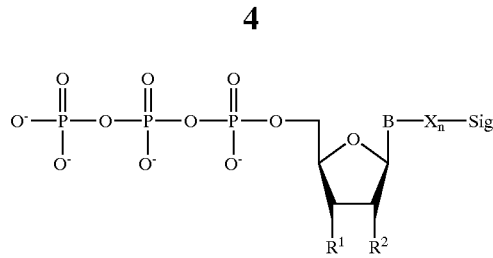

They are produced by starting with unmodified nucleosides in a well-known manner, these i.e. uridine, thymidine and cytidine in the case of pyrimidine nucleosides and the purine nucleosides adenosine and guanosine as well as the corresponding 7-deaza-purine and 7-deaza-8-aza-purine nucleosides, are chemically modified in a suitable manner at C-5 or C-6 (pyrimidine), at C-8 (purine), at C-8 (3-deaza-purine) at C-7 or C-8 (7-deaza-purine) and finally 5'-phosphorylated.

It is expedient that the modified group is composed of a spacer of suitable length and a terminal primary or secondary amino group which can be substituted by suitable activated fluorescent dyes (e.g. in the form of isothiocyanates or N-hydroxysuccinimide esters).

Such fluorescent dyes are used in an activated form, i.e. in a form which reacts well with for example amino groups, preferably as isothiocyanates. After the reaction is completed the fluorophores are covalently bound via NHCS groups to the modified group of the nucleotide.

The phosphorylation of the nucleosides modified in this way is carried out according to methods known in the literature [e.g. Yoshikawa, M. et al. (1967) Tetrah. Lett. 50, 5065] by reaction with phosphoryl trichloride to form the monophosphate and subsequent reaction with pyrophosphoric acid to form the desired 5'-triphosphate. As an alternative a direct modification of the preformed nucleoside 5'-triphosphates is also possible.

The fluorophores are compounds which absorb in the near infrared range i.e. between 600 and 800 nm. Those of 630 nm to 780 nm are preferred such as e.g. carbocyanines.

As already mentioned above, in addition to the method described above of incorporating labelled nucleoside triphosphates using polymerases, a further method is common which is based on the use of labelled oligonucleotides, so-called primers. As already mentioned, the conventional synthesis of these molecules in a multistep reaction is very time-consuming. In this process the signal group must be attached at the 5'-end of the oligomer in an additional step after the oligonucleotide synthesis is completed. Since the actual oligonucleotide synthesis is carried out in automatic synthesizers, it is extremely desirable to also be able to carry out the step of attaching the signal group already in the synthesizer. Since the oligonucleotide synthesis is composed of a stepwise attachment of monomeric building blocks, so-called nucleoside phosphoramidites, it is a further object of the invention to develop a fluorophore phosphoramidite which enables the direct incorporation of the signal group as the last step in automatic oligonucleotide synthesis. Such a NIR-dye-phosphoramidite is hitherto unknown and therefore novel.

The invention is elucidated in more detail by the following examples.

EXAMPLE 1

5-(3-Aminoallyl)-2'-deoxy-uridine-5'-triphosphate

This derivative was synthesized as described by Langer et al in Proc. Natl. Acad. Sci. USA (1981) 78, 6635.

EXAMPLE 2

Anhydro-11-phenoxy-10,12-propylene-3,3,3',3'-tetramethyl-4,5-benzindo-indotricarbocyanin-1-(4-sulfobutyl)-1'-(3-aminopropyl)-thiono-[5-(3-aminoallyl)-2'-deoxyuridine-5'triphosphate]

A solution of 50 mg anhydro-11-phenoxy-10,12-propylene-3,3,3',3'-tetramethyl-4,5-benzindo-1-(4-sulfobutyl)-1'-(3-isothiocyanopropyl)-indotricarbocyanine Na salt (60 μmol) in 1 ml dimethylformamide is added to a solution of 33 mg 5-aminoallyl-dUTP-Li$_4$ (60 μmol) in 2 ml 0.1 M Na-borate buffer, pH 8.5 and the reaction mixture is allowed to stand for about 15 hours at room temperature while protected from light. Afterwards the major portion of the starting materials have reacted according to paper electrophoresis (0.05 M Na-citrate buffer, pH 5). In order to isolate the desired substance, the reaction mixture is diluted with about 50 ml water and the deep-green coloured solution is applied to an ion exchange column containing DEAE Sephadex A-25 in the chloride form. The product is eluted from the column with a linear gradient of water to 1 M LiCl, and the product fractions are concentrated in a vacuum and desalted by means of reversed phase chromatography on RP 18 material. After lyophilization, 6 μmol (10%) of the desired triphosphate is obtained.

Spectral data: Emission$_{max}$ 786 nm, 720 nm (shoulder), 238 nm.

EXAMPLE 3

Anhydro-10,12-propylene-3,3,3',3'-tetramethyl-1,1'-bis(3-sulfobutyl)-indotricarbocyanin-11-(4-amino)-phenoxy-thiono-[8-(5-aminopentylamino)-2'-deoxy-adenosine-5'-triphosphate] ("IRD-dATP")

The derivative is prepared according to the process set forth in example 2 from 38 mg 8-aminopentylamino-dATP (60 μmol) and 50 mg anhydro-10,12-propylene-3,3,3',3'-tetramethyl-1,1'-bis(3-sulfobutyl)-11-(4-isothiocyano)-phenoxy-indotricarbocyanine Na salt (60 μmol). 3 μmol of the compound was obtained.

Spectral data: Emission$_{max}$ 770 nm, 697 nm (shoulder), 279 nm.

EXAMPLE 4

Use of IRD-dATP as a Substrate for T7-DNA Polymerase

3 μg template DNA is incubated for 15 minutes at 37° C. in a mixture of 2 μl reaction buffer (200 mM Tris-HCl, pH 7.5, 100 mM MgCl$_2$, 250 mM NaCl), 1 pM M13/pUC primer and 7 μl H$_2$O.

1 μl DTT (100 mM), 2 μl labelling mixture (10 μM IRD 40-dATP, 1 μM each of dCTP, dGTP and dTTP), 1 μl H$_2$O and 2 μl T7-DNA polymerase (2.5 U/μl) are added for the labelling reaction and it is incubated for 10 minutes at room temperature.

For use in DNA sequencing, a termination reaction is subsequently carried out by addition of the termination mixture (ddATP, ddGTP, ddCTP, ddTTP).

EXAMPLE 5

Anhydro-11-phenoxy-10,12-Propylene-3,3,3',3'-tetra-methyl-4,5-benzindo-indotricarbocyanine-1-(4-sulfo-butyl)-1'-(3-aminopropyl)-thiono-[5-(3-aminoallyl)-uridine-5'-triphosphate The compound was synthesized analogously to example 2 from 5-aminoallyl-UTP (prepared according to example 1) and the corresponding isothiocyanate.

The spectral data correspond to the 2'-deoxy compound of example 2.

EXAMPLE 6

Anhydro-10,12-propylene-3,3,3',3'-tetramethyl-1,1'-bis(3-sulfobutyl)-indo-tricarbocyanin-11-(4-amino) phenoxy-thiono-[5-(3-aminoallyl)-2',3'-dideoxy-uridine-5'-triphosphate] ("IRD-ddUTP")

Step 1: 2',3'-Dideoxy-uridine-5'-triphosphate

The derivative was synthesized via the unstable diazonium derivative starting with the commercially available 2',3'-dideoxy-cytidine-5'-triphosphate (Boehringer Mannheim) by deamination with NaNO$_2$/acetic acid.

Step 2: 5-(3-Aminoallyl)-2',3'-dideoxy-uridine-5'-triphosphate

The compound was prepared analogously to example 1 according to Langer et al supra via the 5-mercury derivative of 2',3'-dideoxy-UTP.

Step 3: "IRD-ddUTP"

The dideoxy derivative was obtained according to example 2 by reacting the 5-aminoallyl-ddUTP with the corresponding isothiocyanate.

The spectral data correspond to those of the 2'-deoxy compound of example 3.

EXAMPLE 7

Anhydro-10,12-propylene-3,3,3',3'-tetramethyl-1,1'-bis(3-sulfopropyl)-indo-tricarbocyanin-11-[(4-ethoxy)phenoxy-O-(2-cyanoethyl)-N,N-diisopropl-phosphoramidite In a 50 ml round bottom flask 425 mg anhydro-11-(4-hydroxyethyl)phenoxy-10,12-propylene-3,3,3',3'-tetramethyl-1,1'-bis(3-sulfopropyl)-indotricarbocyanine-hydroxide in the form of its Na salt (0.5 mmol) is dissolved in 5 ml dry acetonitrile and 0.275 ml ethyldiisopropylamine (1.6 mmol) is added. Subsequently 0.125 ml chloro-β-cyanoethoxy-N,N-diisopropylamino-phosphane are added dropwise within about 3 minutes under nitrogen and while stirring. It is stirred for a further 30 minutes at room temperature, about 10 ml aqueous 5% NaHCO$_3$ solution is then added and it is subsequently extracted twice with, about 10 ml dichloromethane each time. The pooled organic phases are dried over sodium sulfate, the solvent is removed by distillation and the residue is chromatographed on silica gel using the mobile solvent dichloromethane/ethyl acetate/triethyl-amine 45:45:10.

The yield is 480 mg=88.7% of theory.

TLC (silica gel, mobile solvent as above) R$_f$=0.4 $^{31}$p-NMR (d$_6$DMSO): 149 and 153 ppm (2 diastereomers).

What is claimed is:

1. A nucleoside-5'-triphosphate of the general formula

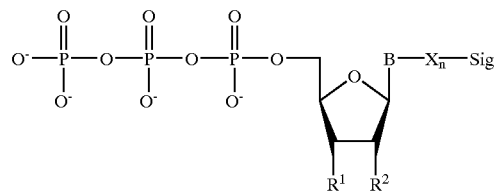

wherein B is a heterocyclic base selected from the group consisting of adenine, guanine, hypoxanthine, 7-deaza-adenine, 7-deaza-guanine, 7-deaza-hypoxanthine, 7-deaza-8-aza-adenine, 7-deaza-8-aza-guanine, 7-deaza-8-aza-hypoxanthine, thymine, cytosine and uracil;

x is a linking group wherein n=4–20 atoms;

Sig is a fluorescent molecule with an excitation wavelength of 650–800 nm; and $R^1$ and $R^2$ each represent H or OH.

2. Method for detecting a target nucleic acid molecule, comprising:
   (a) contacting said target nucleic acid molecule with a complementary nucleic acid probe under conditions favoring hybridization between said target nucleic acid sequence and said complementary probe, wherein said complimentary nucleic acid probe is characterized as a nucleic acid sequence having incorporated therein at least one labelled nucleoside 5'-triphosphate according to claim 1, and
   (b) detecting said labelled complimentary nucleic acid probe as a determinant of said target nucelic acid molecule.

3. The method of claim 2, wherein said labelled nucleic acids are detected by hybridization.

4. The method of claim 3, wherein said hybridization is carried out on membranes or in solution.

5. The method of claim 2, wherein the labelled nucleic acids are detected using laser diodes and detectors.

6. The method of claim 2, which further comprises the step of sequencing said labelled nucleic acids.

7. The compound of claim 1, wherein:

x is a linking group wherein n=10–15 atoms and Sig is a carbocyanine of the general formula:

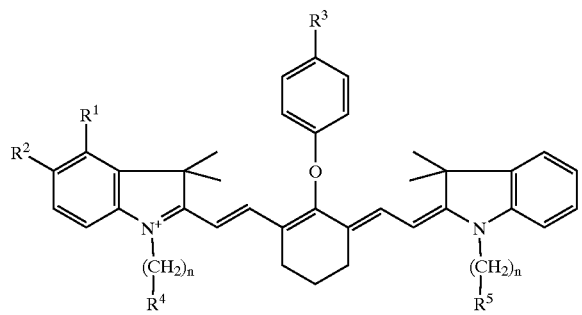

wherein $R^1$ and $R^2$=H or together represent a phenyl residue;

$R^3$=H if linkage with the nucleotide is via the $R^4$ position, or $R^3$=—NHCS— if linkage is via the $R^3$ position; and $R^4$ and $R^5$ each denote alkylsulfonyl wherein n=3–5; or $R^4$—NHCS— wherein n=3–8 and $R^5$=alkylsulfonyl wherein n=3–5 if linkage is via the $R^4$ position.

8. A method of detecting nucleic acids comprising labelling nucleic acids with the compound of claim 7, and detecting said labelled nucleic acids.

9. The method of claim 8, wherein said labelled nucleic acids are detected by hybridization.

10. The method of claim 9, wherein said hybridization is carried out on membranes or in solution.

11. The method of claim 8, wherein the labelled nucleic acids are detected using laser diodes and detectors.

12. The method of claim 8, which further comprises the step of sequencing said labelled nucleic acids.

13. An oligonucleoide which comprises the nucleoside molecule of claim 1.

14. The nucleoside 5'-triphosphate of claim 1, wherein said triphosphate is selected from the group consisting of anhydro-11-phenoxy-10,12-propylene-3,3,3',3'-tetramethyl-4,5-benzindo-indotricarbocyanin-1-(4-sulfobutyl)-1'-(3-aminopropyl)-thiono-[5-(3-aminoallyl)-2'-deoxyuridine-5'-triphosphate]4anhydro-10,12-propylene-3,3,3',3'-tetramethyl-1,1'-bis(3-sulfobutyl)-indotricarbocyanin-11-(4-amino)-phenoxy-thione-[8-(5-aminoapentylamino)-2'-deoxyadenosine-5'-triphosphate]; anhydro-11-phenoxy-10,12-propylene-3,3,3',3'-tetramethyl-4,5-benzindo-indotricarbocyanine-1-(4-sulfobutyl)-1'-(3-aminopropyl)-thiono-[5-(3-aminoallyl)-uridine-5'-triphosphate]; anhydro-10,12-propylene-3,3,3',3'-tetramethyl-11'-bis(3-sulfobutyl)-indo-tricarbocyanin-11-(4-amino)-phenoxy-thiono-[5-(3-aminoaallyl)-2',3'-dideoxyuridine-5'-triphosphate]; and anhydro-10,12-propylene-3,3,3',3'-tetramethyl-1,1'-bis(3-sulfopropyl)-indo-tricarbocyanin-11-(4-ethoxy)phenoxy-o-(2-cyanoethyl)-N,N-diisopropyl-phosphoramidite.

* * * * *

UNITED STATES PATENT AND TRADEMARK OFFICE
CERTIFICATE OF CORRECTION

PATENT NO.    : 6,573,374 B1
DATED         : June 3, 2003
INVENTOR(S)   : Klaus Muehlegger et al.

It is certified that error appears in the above-identified patent and that said Letters Patent is hereby corrected as shown below:

<u>Title page,</u>
Item [75], Inventors, please add -- Lyle R. Middendorf -- on the Inventors' list.

Signed and Sealed this

Twenty-fifth Day of May, 2004

JON W. DUDAS
*Acting Director of the United States Patent and Trademark Office*